US010548547B2

(12) United States Patent
Matsuzawa (10) Patent No.: US 10,548,547 B2
(45) Date of Patent: Feb. 4, 2020

(54) X-RAY COMPUTED TOMOGRAPHY APPARATUS

(71) Applicant: Toshiba Medical Systems Corporation, Otawara-shi (JP)

(72) Inventor: Yohei Matsuzawa, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 729 days.

(21) Appl. No.: 14/730,713

(22) Filed: Jun. 4, 2015

(65) Prior Publication Data

US 2015/0265230 A1    Sep. 24, 2015

Related U.S. Application Data

(63) Continuation of application No. PCT/JP2013/082629, filed on Dec. 4, 2013.

(30) Foreign Application Priority Data

Dec. 4, 2012 (JP) .................. 2012-265809
Dec. 4, 2013 (JP) .................. 2013-250919

(51) Int. Cl.
*A61B 6/00* (2006.01)
*A61B 6/03* (2006.01)

(52) U.S. Cl.
CPC ............ *A61B 6/4447* (2013.01); *A61B 6/035* (2013.01)

(58) Field of Classification Search
CPC .................................................... A61B 6/035
See application file for complete search history.

(56) References Cited

U.S. PATENT DOCUMENTS

| 5,960,054 A | 9/1999 | Freeman et al. |
| 2002/0009174 A1* | 1/2002 | Sasaki .................... A61B 6/035 378/4 |
| 2002/0031201 A1 | 3/2002 | Suzuki et al. |

(Continued)

FOREIGN PATENT DOCUMENTS

| JP | 03-178643 A | 8/1991 |
| JP | 10-314160 A | 12/1998 |
| JP | 11-226002 A | 8/1999 |

(Continued)

OTHER PUBLICATIONS

International Search Report dated Mar. 11, 2014 for PCT/JP2013/082629 filed on Dec. 4, 2013 with English Translation.

(Continued)

*Primary Examiner* — Hoon K Song
(74) *Attorney, Agent, or Firm* — Oblon, McClelland, Maier & Neustadt, L.L.P.

(57) ABSTRACT

The rigidity of a gantry is efficiently increased in a limited space. A gantry rotating unit has a structure on which an X-ray tube and an X-ray detector can be mounted. A main frame supports the gantry rotating unit so as to allow it to rotate around a rotation axis. A base stand supports the main frame from the floor surface. Gantry arms are coupled to one of half portions of the main frame which are one of half portions divided by a horizontal axis and the base stand. Reinforcing frames are coupled to the other of the half portions of the main frame and the gantry arms.

11 Claims, 9 Drawing Sheets

(56) References Cited

U.S. PATENT DOCUMENTS

2010/0266105 A1 10/2010 Sharpless et al.
2014/0016758 A1* 1/2014 Theiss .................. A61B 6/035
　　　　　　　　　　　　　　　　　　　　　　　378/197

FOREIGN PATENT DOCUMENTS

| JP | 11-276471 A | 10/1999 |
| JP | 2000-116644 A | 4/2000 |
| JP | 2000-237181 | 9/2000 |
| JP | 2002-253543 A | 9/2002 |
| JP | 2003-093379 A | 4/2003 |
| JP | 2010-63775 A | 3/2010 |
| JP | 2012-50735 A | 3/2012 |

OTHER PUBLICATIONS

Written Opinion dated Mar. 11, 2014 for PCT/JP2013/082629 filed on Dec. 4, 2013.

* cited by examiner

X-RAY COMPUTED TOMOGRAPHY APPARATUS

CROSS-REFERENCE TO RELATED APPLICATIONS

This application is a Continuation Application of PCT Application No. PCT/JP2013/082629, filed Dec. 4, 2013 and based upon and claims the benefit of priority from the Japanese Patent Application No. 2012-265809, filed Dec. 4, 2012, and No. 2013-250919, filed Dec. 4, 2013, the entire contents of all of which are incorporated herein by reference.

FIELD

Embodiments described herein relate generally to an X-ray computed tomography apparatus.

BACKGROUND

An X-ray computed tomography apparatus is preferably designed to minimize the vibration of the gantry which is generated when the gantry rotates, in order to improve image quality. To scan a moving organ such as the heart of a human body with good image quality, it is necessary to rotate the gantry at high speed. However, as the rotational speed of the gantry increases, the vibration of the gantry increases.

As measures to reduce vibration accompanying the rotation of the gantry, there are known a method of adjusting the rotation/forward-backward balance of the gantry rotating unit by using an adjustment weight, a method of increasing the rigidity of the frame of each gantry portion, and the like.

The market needs concerning recent X-ray computed tomography apparatuses are to reduce the outer shape sizes and weights of X-ray computed tomography apparatuses which can rotate at high speed. That is, there are no market needs to simply increase the sizes and weights of the frames of the respective gantry portions to increase the rigidity of the frames.

DETAILED DESCRIPTION

In general, according to one embodiment, an X-ray computed tomography apparatus includes an annular rotating unit, a main frame, a base stand, a gantry arm, and a coupling frame. The annular rotating unit is on which an X-ray tube and an X-ray detector are configured to be mounted. The main frame is configured to support the rotating unit so as to allow the rotating unit to rotate about a rotation axis. The base stand is configured to support the main frame from a floor surface. The gantry arm is coupled to the base stand and one of half portions of the main frame divided by a horizontal axis perpendicular to the rotation axis. The coupling frame is coupled to the gantry arm and the other of the half portions of the main frame.

An X-ray computed tomography apparatus according to this embodiment will be described below with reference to the accompanying drawings.

Figure 1:
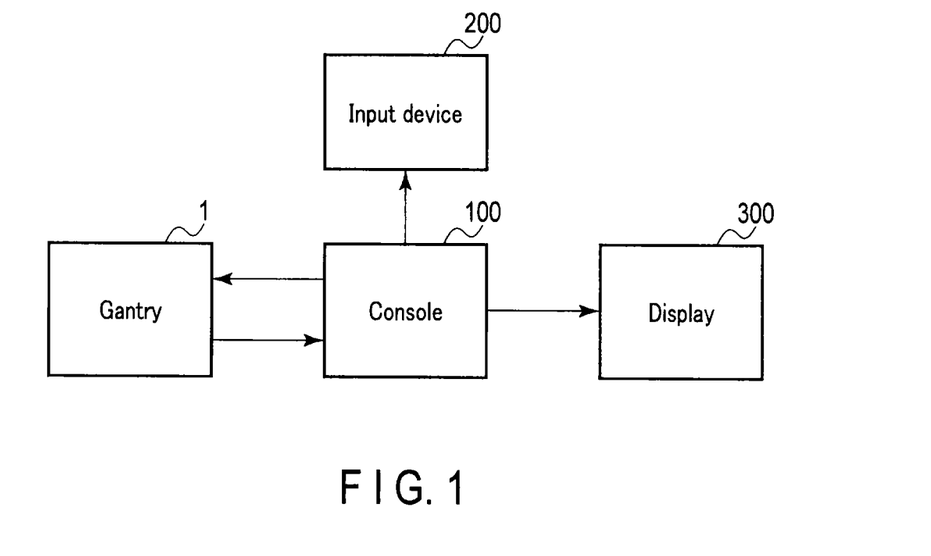
FIG. 1 is a block diagram showing the arrangement of an X-ray computed tomography apparatus according to an embodiment.

FIG. 1 is a block diagram showing the arrangement of an X-ray computed tomography apparatus according to this embodiment. As shown in FIG. 1, the X-ray computed tomography apparatus according to the embodiment includes a gantry 1 and a console 100. The gantry 1 is installed in a CT imaging room in a hospital or the like. The console 100 is installed in the CT imaging room or a control room or the like adjacent to the CT imaging room. The console 100 controls the gantry 1 in accordance with instructions and the like from the operator via an input device 200. The gantry 1 executes X-ray CT imaging under the control of the console 100. The gantry 1 is equipped with an X-ray tube and an X-ray detector arranged to face each other through an object. The gantry 1 acquires raw data representing the attenuation of X-rays by repeating X-ray irradiation and X-ray detection at high speed while rotating the X-ray tube and the X-ray detector around the rotation axis. The gantry 1 transmits the acquired raw data to the console 100. The console 100 reconstructs a CT image expressing the spatial distribution of X-ray attenuation coefficients in the object based on the raw data. The console 100 displays the CT image on a display 300.

Figure 2:
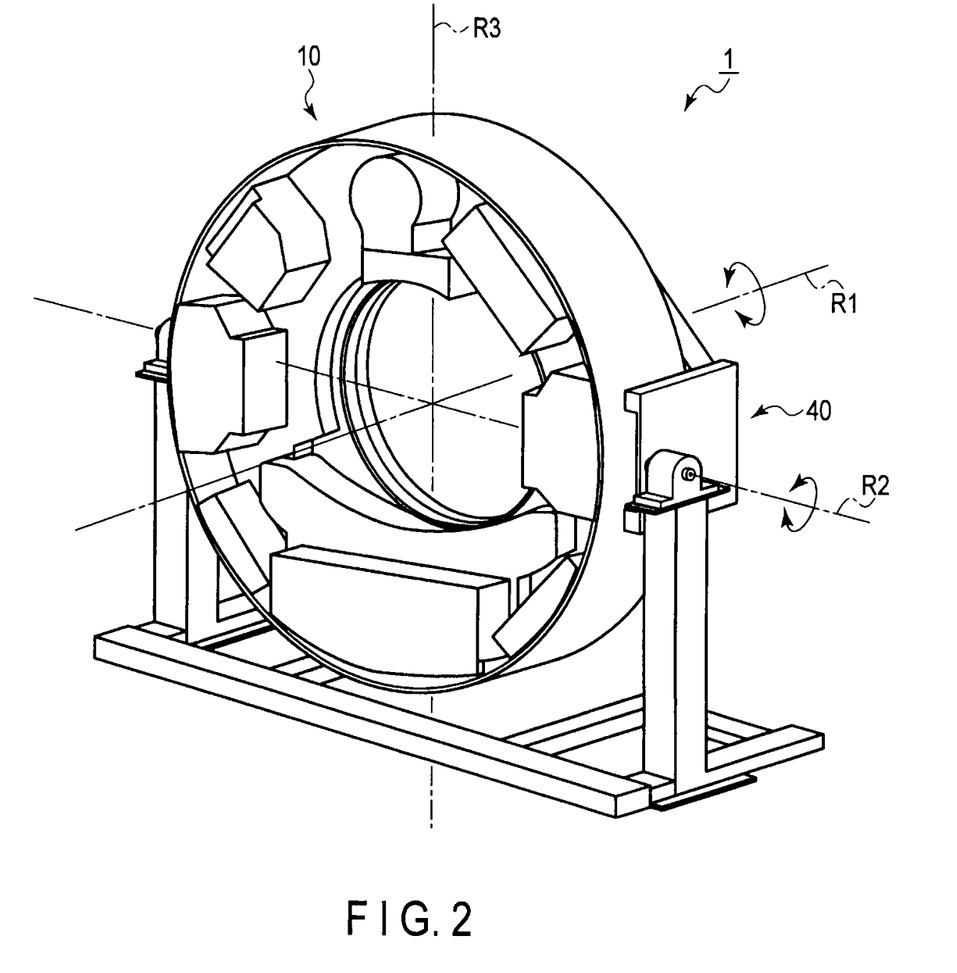
FIG. 2 is a schematic perspective view of a gantry in FIG. 1.
Figure 3:
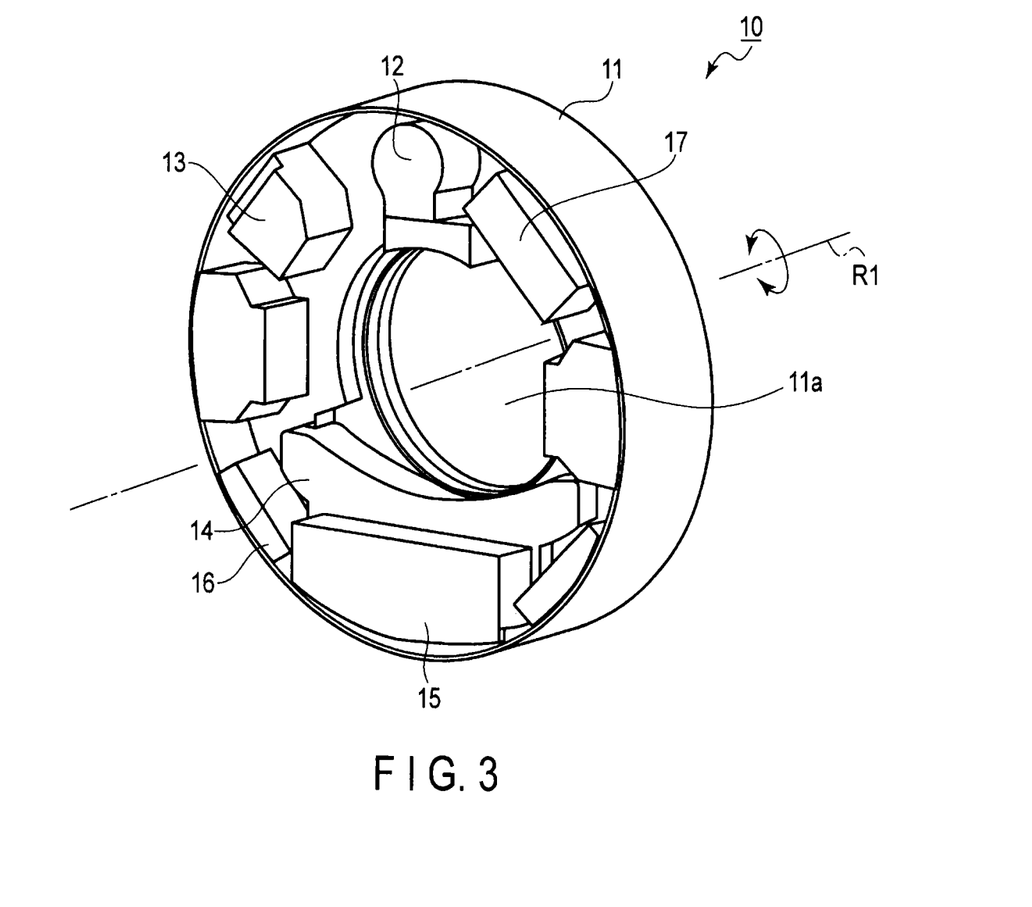
FIG. 3 is a schematic perspective view of a gantry rotating unit in FIG. 2.
Figure 4:
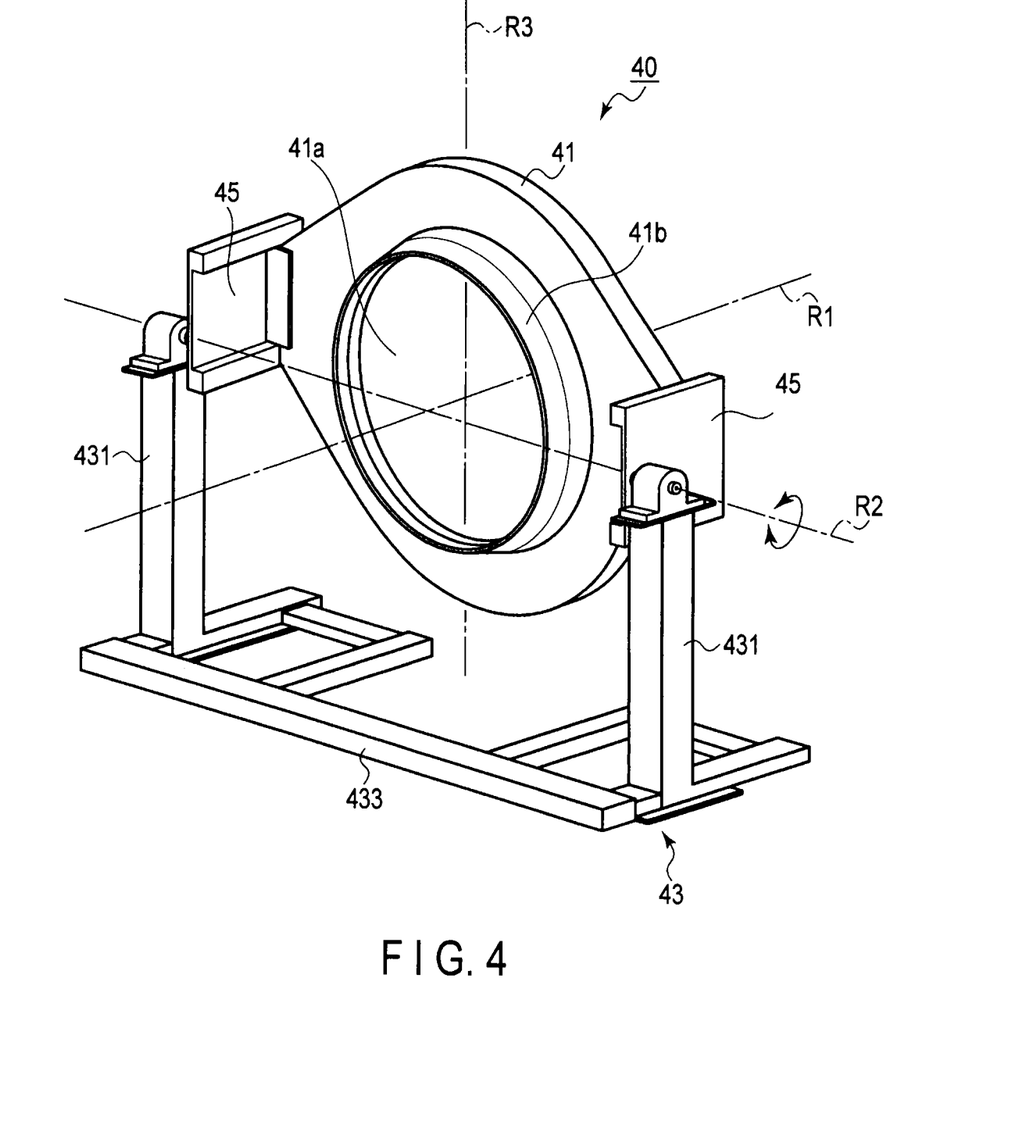
FIG. 4 is a schematic perspective view of a gantry fixing unit in FIG. 2.

FIG. 2 is a schematic perspective view of the gantry 1. Note that FIG. 2 shows the gantry 1 from which the cover is detached. As shown in FIG. 2, the gantry 1 includes a gantry rotating unit 10 and a gantry fixing unit 40. FIG. 3 is a schematic perspective view of the gantry rotating unit 10. FIG. 4 is a schematic perspective view of the gantry fixing unit 40.

As shown in FIGS. 2 and 3, the gantry rotating unit 10 includes a rotating frame 11 having a nearly cylindrical shape, with an opening 11a being formed in the center. A hole or recess portion is formed in the rotating frame 11 to mount various types of devices such as an X-ray tube 12, a high voltage generator 13, an X-ray detector 14, a data acquisition circuit 15, a data transmitter 16, and a cooling device 17. The rotating frame 11 is a metal frame formed from a metal such as aluminum. Various types of devices such as the X-ray tube 12, the high voltage generator 13, the X-ray detector 14, the data acquisition circuit 15, the data transmitter 16, and the cooling device 17 operate upon receiving power from the gantry fixing unit 40. The X-ray tube 12 and the X-ray detector 14 are mounted on the rotating frame 11 so as to face each other through the opening 11a. The high voltage generator 13 applies a high voltage to the X-ray tube 12, and supplies a filament current to the X-ray tube 12. Upon receiving the high voltage and the filament current from the high voltage generator 13, the X-ray tube 12 generates X-rays. The X-ray detector 14 detects the X-rays generated from the X-ray tube 12 and generates an electrical signal corresponding to the intensity of the detected X-rays. The data acquisition circuit 15 converts the electrical signal generated by the X-ray detector 14 into raw data by A/D-converting the electrical signal. The raw data is transmitted to the console 100 via the data transmitter 16. The cooling device 17 cools the X-ray tube 12.

As shown in FIG. 4, the gantry fixing unit 40 includes a main frame 41, a base stand 43, and gantry arms 45. The main frame 41 is a metal frame formed from a metal such as aluminum. An opening 41a is formed in the center of the main frame 41. The main frame 41 supports, at an edge portion 41b, the gantry rotating unit 10 so as to allow it to rotate about a rotation axis R1. The gantry rotating unit 10 rotates about the rotation axis R1 upon receiving a driving signal from a driving device (not shown).

The base stand 43 is installed on the floor surface of a CT imaging room. The base stand 43 supports the main frame 41 at a distance from the floor surface. The base stand 43 includes, for example, two upright frames 431 and a connection frame 433. The two upright frames 431 are mounted on the two side surfaces of the main frame 41 and installed upright on the floor surface. The connection frame 433 connects the two upright frames 431 to strength the support of the main frame 41 by the two upright frames 431. The base stand 43 is formed from a metal such as aluminum.

The two gantry arms 45 support the main frame 41 so as to allow it to tilt around a horizontal axis R2 which is perpendicular to the rotation axis R1 and parallel to the floor surface. The two gantry arms 45 are arranged such that the gantry rotating unit 10 intersects the horizontal axis R2, and hence support the main frame 41 so as to separate it from the horizontal axis R2 along the rotation axis R1. Each gantry arm 45 is mounted at the upper portion of the base stand 43 to couple the base stand 43 to the main frame 41. As the main frame 41 tilts, a vertical axis R3 perpendicular to the rotation axis R1 and the horizontal axis R2 tilts with respect to the floor surface. The gantry arms 45 tilt the main frame 41 upon receiving a driving signal from a driving device (not shown) in the cover. The gantry arms 45 are formed from a metal such as aluminum. Note that the respective portions of the gantry fixing unit 40 are typically designed so as to locate the horizontal axis R2 at a height of about 1,000 mm from the floor surface.

As the gantry rotating unit 10 rotates about the rotation axis R1 at high speed, forces are applied to the upper and lower portions of the main frame 41 in the direction of the rotation axis R1. With reductions in the size and weight of the main frame 41, the strength of the main frame 41 decreases. As a consequence, forces in the direction of the rotation axis R1 will bend the upper and lower portions of the main frame 41 in the direction of the rotation axis R1. In addition, as the main frame 41 deforms, forces are applied to the gantry arms 45 in the direction of the horizontal axis R2. The forces in the direction of the horizontal axis R2 will bend the gantry arms 45 in the direction of the horizontal axis R2.

The gantry fixing unit 40 according to this embodiment includes reinforcing frames for preventing the deformation of the main frame 41 and the gantry arms 45 upon high-speed rotation of the gantry rotating unit 10. The detailed structure of the gantry fixing unit 40 according to the embodiment will be described below.

Figure 5:
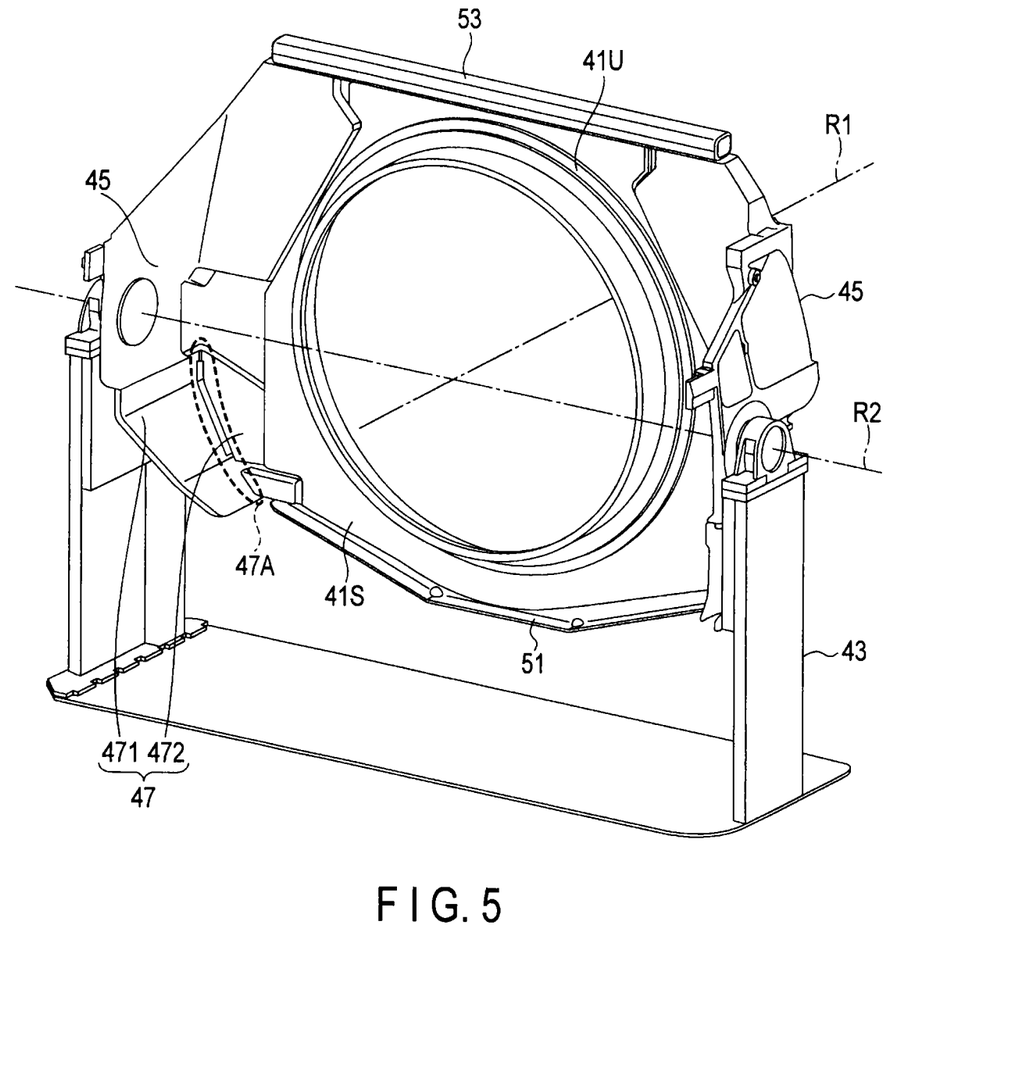
FIG. 5 is a perspective view showing the gantry fixing unit in FIG. 1 when viewed from the front surface side.
Figure 6:
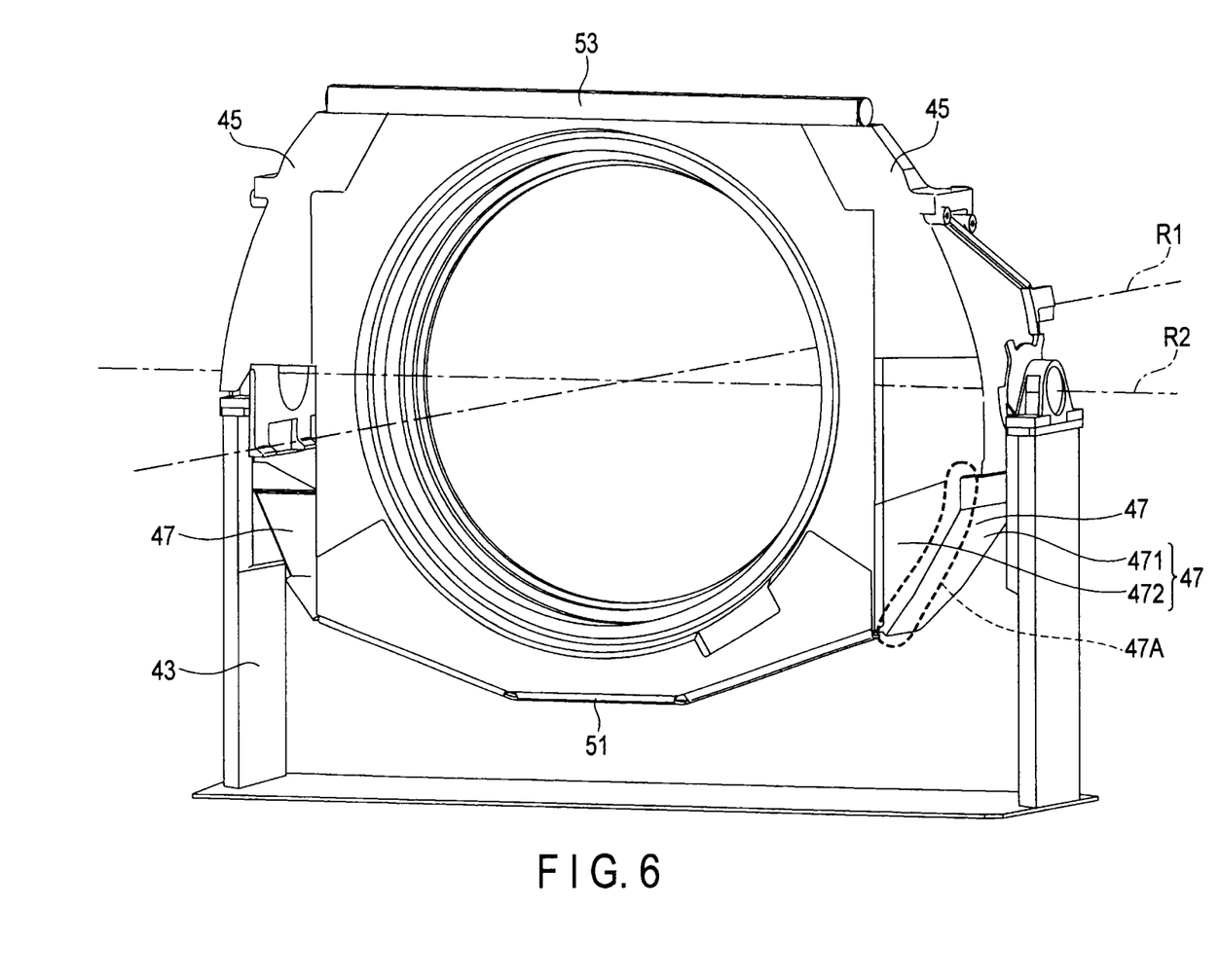
FIG. 6 is a perspective view showing the gantry fixing unit in FIG. 1 when viewed from the rear surface side.

FIG. 5 is a perspective view showing the gantry fixing unit 40 when viewed from the front surface side. FIG. 6 is a perspective view showing the gantry fixing unit 40 when viewed from the rear surface side. Assume that the front surface is the surface on which the gantry rotating unit 10 of the main frame 41 is arranged. As shown in FIGS. 5 and 6, the gantry arms 45 are coupled to an upper half portion 41U and the base stand 43. The upper half portion 41U are one of the two parts divided by the horizontal axis R2, of the main frame 41. More specifically, each gantry arm 45 has a bent structure to prevent interference with the gantry rotating unit 10. Having the bent structure allows each gantry arm 45 to be coupled to the base stand 43 and the upper half portion 41U while avoiding contact with the gantry rotating unit 10. In order to increase the rigidity of the main frame 41, the gantry arms 45 are preferably coupled to not only the side surface edge portion of the upper half portion 41U of the main frame 41 but also the front surface of the upper half portion 41U. Alternatively, the gantry arms 45 may be coupled to not only the side surface edge portion of the upper half portion 41U of the main frame 41 but also the rear surface of the upper half portion 41U. Furthermore, in order to further increase the rigidity, the gantry arms 45 may be coupled to not only the side surface edge portion of the upper half portion 41U of the main frame 41 but also the front and rear surfaces of the upper half portion 41U.

A lower half portion 41S of the main frame 41 and each gantry arm 45 are coupled through a reinforcing frame 47. The lower half portion 41S are the other parts of the two parts divided by the horizontal axis R2. As described above, the respective portions of the gantry fixing unit 40 are typically designed such that the horizontal axis R2 is located at a height of about 1,000 mm from the floor surface. Therefore, the upper half portion 41U is a portion of the main frame 41 which is located 1,000 mm and more away from the floor surface, and the lower half portion 41S is a portion of the main frame 41 which is located 1,000 mm or less away from the floor surface.

The reinforcing frames 47 are frames formed from a metal. The reinforcing frames 47 are preferably formed from a metal having higher strength than the main frame 41. If, for example, the main frame 41 is formed from aluminum, the reinforcing frames 47 are preferably formed from a metal such as iron. Note that if sufficient strength can be ensured, the reinforcing frames 47 may be formed from the same material as that for the main frame 41. The reinforcing frames 47 are individually formed by sheet-metal welding. Alternatively, the reinforcing frames 47 may be integrally formed with the main frame 41 and the gantry arms 45 in a mold. The manner of integral formation to be used is not limited to integral formation using a mold and may include integrating the main frame 41, the reinforcing frames 47, and the gantry arms 45, which are individually formed, by welding. As will be described later, each reinforcing frame 47 has a bent structure to avoid interference with the gantry rotating unit 10. Having the bent structures allows the reinforcing frame 47 to be coupled to the gantry arms 45 and the lower half portion 41S while avoiding contact with the gantry rotating unit 10.

Note that, as shown in FIG. 6, only the reinforcing frames 47 and the gantry arms 45 may be integrally formed. Gantry arms 45' in FIG. 6 have portions (to be referred to as gantry arm portions hereinafter) 45U corresponding to the gantry arms 45 and portions (to be referred to as reinforcing frame portions hereinafter) 47U corresponding to the reinforcing frames 47. The gantry arm portions 45U couple the upper half portion 41U to the base stand 43. The reinforcing frame portions 47U couple the lower half portion 41S to the gantry arm portions 45U. The gantry arm portions 45U have the same structure as that of the gantry arms 45 except that they are integrally formed with the reinforcing frame portions 47U. On the other hand, the reinforcing frame portions 47U have the same structure as that of the reinforcing frames 47 except that they are integrally formed with the gantry arm portions 45U.

Figure 7:
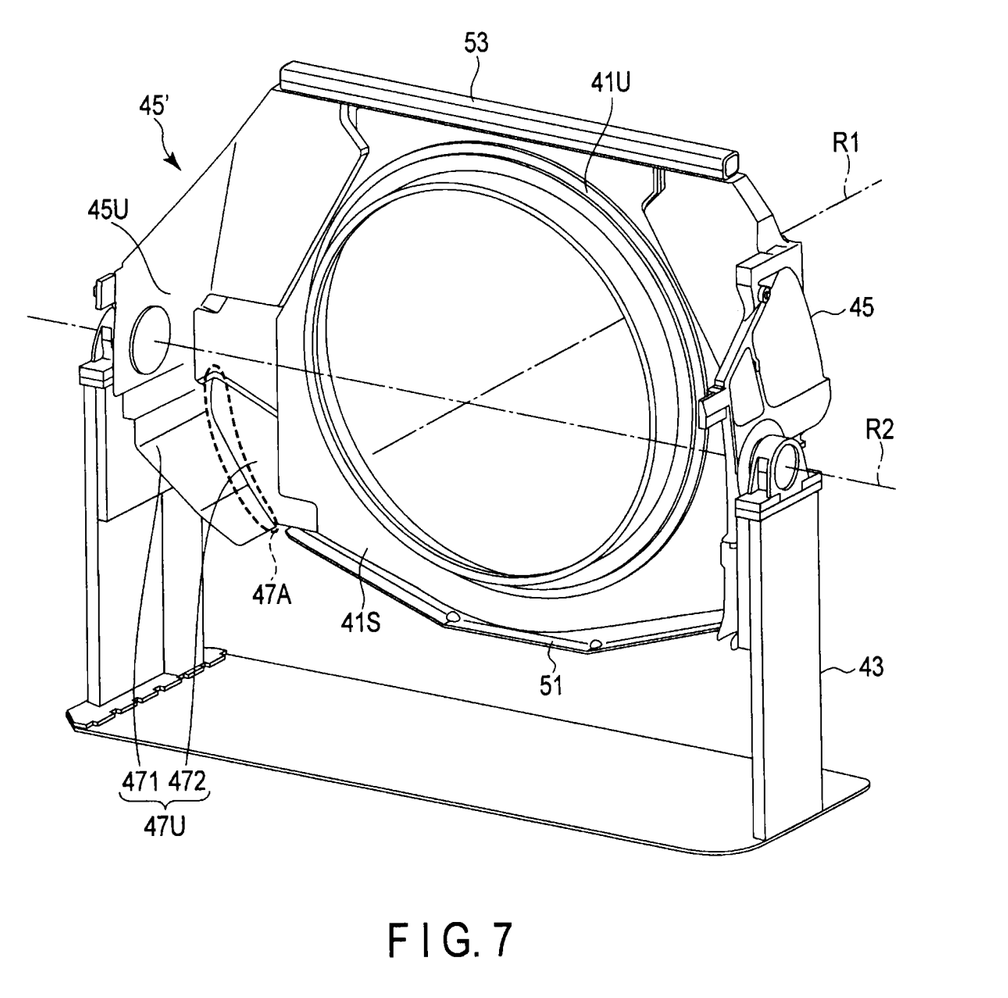
FIG. 7 is a perspective view showing another gantry fixing unit in FIG. 1 when viewed from the front surface side.
Figure 8:
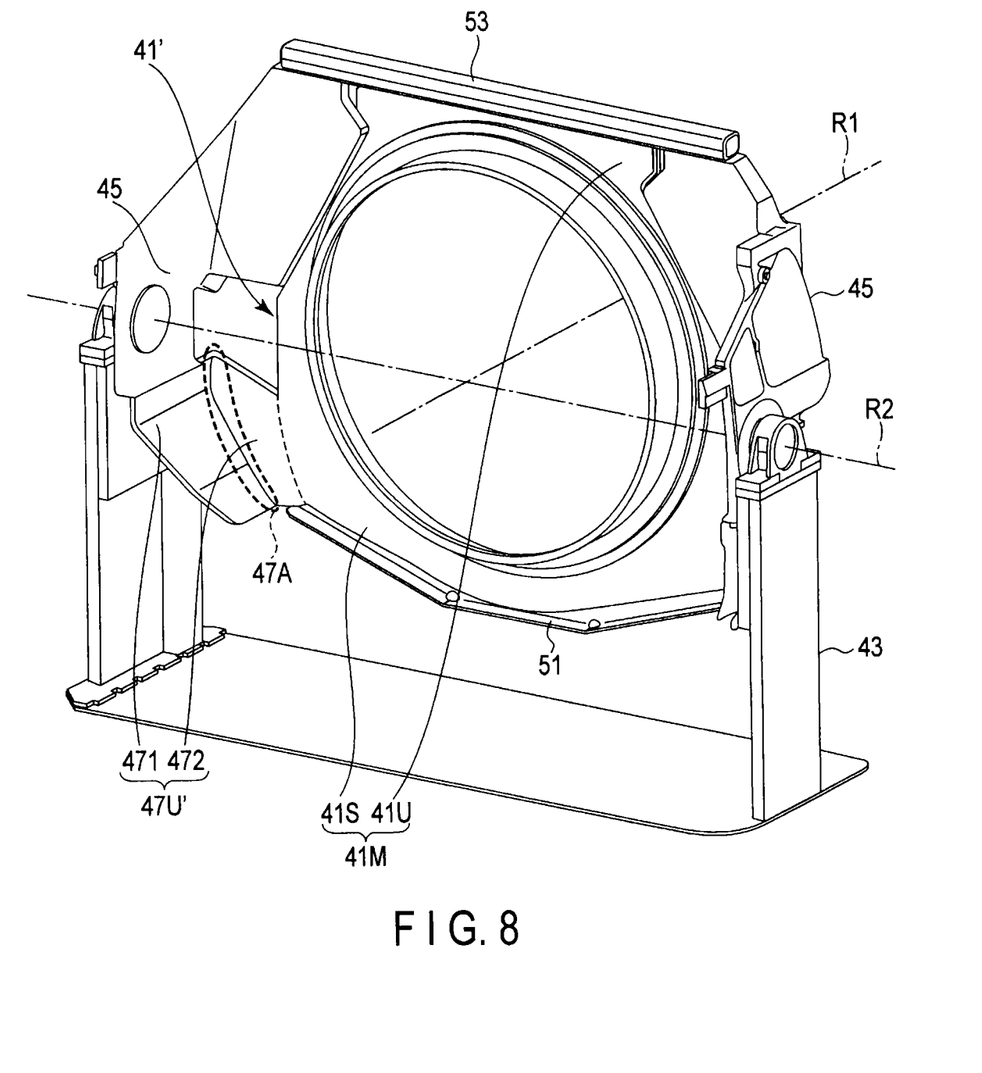
FIG. 8 is a perspective view showing another gantry fixing unit in FIG. 1 when viewed from the front surface side.

Alternatively, as shown in FIG. 7, only the reinforcing frames 47 and the main frame 41 may be integrally formed. A main frame 41' in FIG. 8 has a portion (to be referred to as a main frame portion hereinafter) 41M corresponding to the main frame 41 and portions (to be referred to as reinforcing frame portions hereinafter) 47U' corresponding to the reinforcing frames 47. The upper half portion 41U of the main frame portion 41M is coupled to the gantry arms 45. The lower half portion 41S of the main frame portion 41M is coupled to the gantry arms 45. More specifically, the reinforcing frame portions 47U' of the lower half portion 41S have bent structures, and the gantry arms 45 and portions of the main frame 41 are coupled to each other through the reinforcing frame portions 47U'. The main frame portion 41M has the same structure as that of the main frame 41 except that it is integrally formed with the reinforcing frame portions 47U'. On the other hand, the reinforcing frame portions 47U' have the same structure as that of the reinforcing frames 47 except that they are integrally formed with the main frame portion 41M. For the sake of a concrete description, assume that the main frame 41, the reinforcing frames 47, and the gantry arms 45 are individually formed.

As shown in FIGS. 5 and 6, the gantry arms 45 and the reinforcing frames 47 are coupled to each other with, for example, fastening tools such as screws. Likewise, the main frame 41 and the reinforcing frames 47 are coupled to each other with, for example, fastening tools such as screws. To facilitate coupling to the reinforcing frames 47, coupling portions 45K between the gantry arms 45 and the reinforcing frames 47 and coupling portions 41K between the main frame 41 and the reinforcing frames 47 preferably have planar shapes.

More specifically, each reinforcing frame 47 is preferably coupled to the lower end portion of the gantry arm 45 and the side surface edge portion of the lower half portion 41S of the main frame 41. However, the coupling portion of each reinforcing frame 47 is not limited to this, and may be any place to which the reinforcing frame 47 can be coupled. For example, each reinforcing frame 47 may be coupled to the inside surface or outside surface of the gantry arm 45 instead of the lower end portion of the gantry arm 45. In addition, each reinforcing frame 47 may be coupled to the front surface or rear surface of the lower half portion 41S instead of the side surface edge portion of the lower half portion 41S of the main frame 41. It is possible to further increase the rigidity of the main frame 41 by coupling the reinforcing frames 47 to not only the side surface edge portion of the lower half portion 41S of the main frame 41 but also the front or rear surface.

Figure 9:
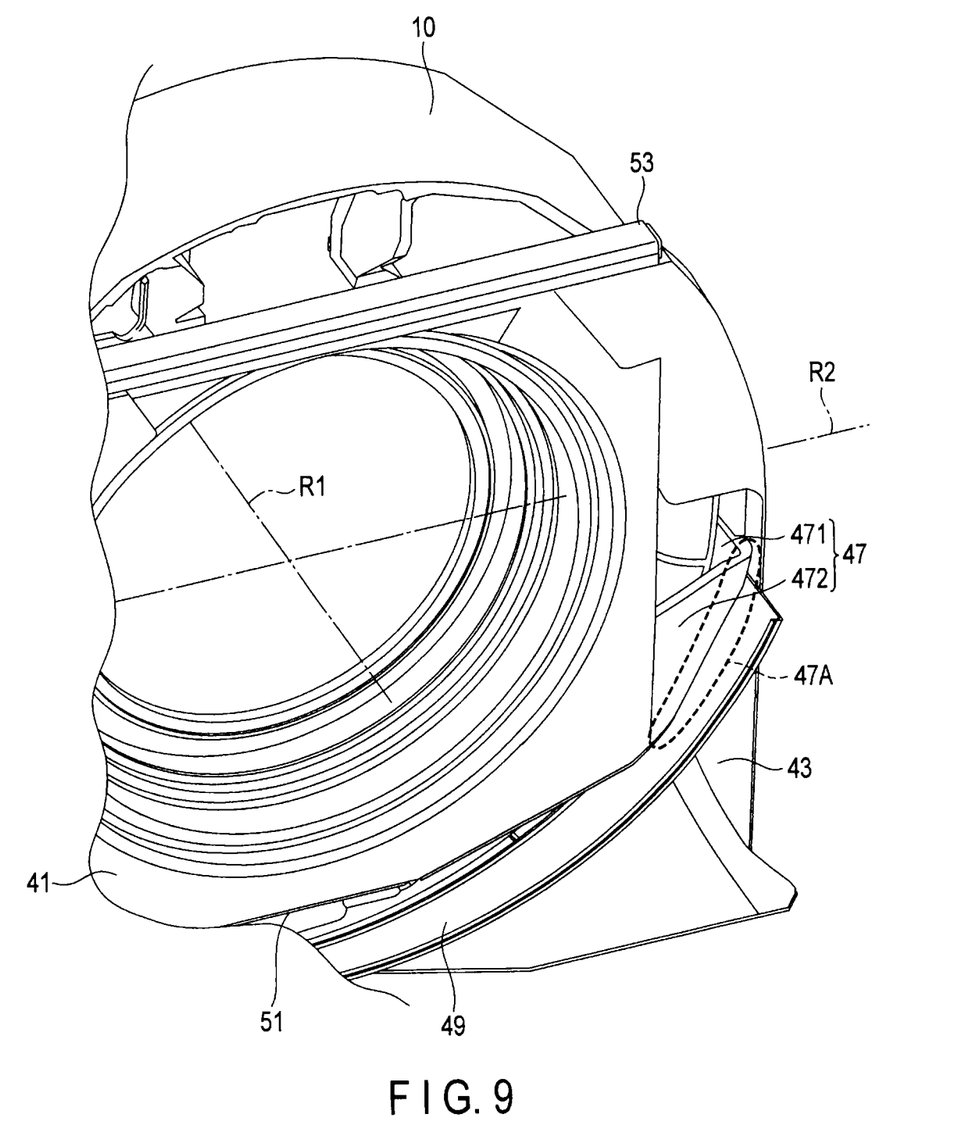
FIG. 9 is a partially cutaway perspective view of the gantry on which the gantry rotating unit and the gantry fixing unit in FIG. 1 are mounted when viewed from the rear surface side.

The positional relationship between each reinforcing frame 47 and the gantry rotating unit 10 will be described next with reference to FIG. 9. FIG. 9 is a partially cutaway perspective view showing the gantry fixing unit 40 on which the rotating frame 11 is mounted, when viewed from the rear surface side. As shown in FIG. 9, a cover (to be referred to as a main under cover hereinafter) 49 for covering the half portion of the rotating frame 11 which is located below the vertical axis R2 is provided. The main under cover 49 is mounted to prevent the gantry rotating unit 10 from being seen from outside when the rotating frame 11 and the main frame 41 are tilted. The main under cover 49 is connected to the gantry arms 45 directly or via a structure. The reinforcing frames 47 are provided between the main under cover 49 and the rotating frame 11 (i.e., the gantry rotating unit 10).

If each reinforcing frame 47 has a linear shape (flat shape), the main frame 41 is linearly connected to the base stand 43. In this case, the gantry rotating unit 10 contacts the reinforcing frames 47. This makes it impossible to mount the gantry rotating unit 10 on the main frame 41. For this reason, each reinforcing frame 47 has a bent portion 47A which can avoid interference with the gantry rotating unit 10. More specifically, each reinforcing frame 47 has a structure in which a first portion 471 and a second portion 472 intersect at a right angle at the bent portion 47A. The first portion 471 is coupled to the gantry arm 45 so as to be smoothly connected to the inside surface of the gantry arm 45. The second portion 472 is coupled to the main frame 41 so as to be smoothly connected to the front surface of the main frame 41. The first portion 471 and the second portion 472 are coupled to each other so as to intersect each other. Since each reinforcing frame 47 has the bent portion 47A, it is possible to accommodate the reinforcing frame 47 between the gantry rotating unit 10 and the main under cover 49 while preventing interference between the reinforcing frame 47 and the gantry rotating unit 10.

In order to further increase the strength of the main frame 41, other reinforcing frames 51 and 53 may be provided on the outside of the main frame 41. The reinforcing frame 51 is mounted on the edge portion of the lower half portion 41S of the main frame 41. Mounting the reinforcing frame 51 on the edge portion of the lower half portion 41S can prevent the deformation of the lower half portion 41S in the direction of the rotation axis R1 accompanying the rotation of the gantry rotating unit 10. The reinforcing frame 53 is mounted on the edge portion of the upper half portion 41U of the main frame 41 and the edge portions of the gantry arms 45. Mounting the reinforcing frame 51 on the edge portion of the upper half portion 41U can prevent the deformation of the upper half portion 41U in the direction of the rotation axis R1 accompanying the rotation of the gantry rotating unit 10. The reinforcing frames 51 and 53 are preferably formed from a metal having higher strength than the main frame 41 If, for example, the main frame 41 is formed from aluminum, the reinforcing frames 51 and 53 are preferably formed from a metal such as iron. Note that if sufficient strength can be ensured, the reinforcing frames 51 and 53 may be formed from the same material as that for the main frame 41.

Modification

In the above embodiment, the gantry arms 45 are coupled to the upper half portion 41U of the main frame 41, and the reinforcing frames 47 are coupled to the lower half portion 41S. However, this embodiment is not limited to this. For example, the gantry arms 45 may be coupled to the lower half portion 41S of the main frame 41, and the reinforcing frames 47 may be coupled to the upper half portion 41U of the main frame 41.

Effects

As described above, the X-ray computed tomography apparatus according to this embodiment includes at least the gantry rotating unit 10, the main frame 41, the base stand 43, the gantry arms 45, and the reinforcing frames 47. The gantry rotating unit 10 has a structure on which the X-ray tube 12 and the X-ray detector 14 can be mounted. The main frame 41 supports the gantry rotating unit 10 so as to allow it to rotate about the rotation axis R1. The base stand 43 supports the main frame 41 at a distance from the floor surface. The gantry arms 45 support the main frame 41 so as to allow it to tilt around the horizontal axis R2 perpendicular to the rotation axis R1, and are coupled to one of the half portions of the main frame 41 divided by the horizontal axis R2 and the base stand 43. The reinforcing frames 47 are coupled to the other of the half portions of the main frame 41 and the gantry arms 45.

Coupling the reinforcing frames 47 to a half portion of the main frame 41 and the gantry arms 45 as in the above arrangement can suppress the vibration and deformation of the main frame 41 and the gantry arms 45 accompanying the high-speed rotation of the gantry rotating unit 10 around the rotation axis R1. In addition, since the reinforcing frames 47 are small-size structures, mounting the reinforcing frames 47 on the gantry 1 will not change the outer shape size of the gantry 1 as a whole and will not make any large change in weight. Therefore, the reinforcing frames 47 can increase the rigidity of the gantry 1 spatially efficiently, and suppress vibration and deformation accompanying the high-speed rotation of of the gantry rotating unit 10.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray computed tomography apparatus, comprising:
   an annular rotating unit on which an X ray tube and an X ray detector are configured to be mounted;
   a first frame configured to support the rotating unit so as to allow the rotating unit to rotate about a rotation axis;
   a base stand configured to support the first frame from a floor surface;
   a gantry arm coupled to the base stand and one of half portions of the first frame divided by a horizontal axis perpendicular to the rotation axis; and
   a second frame coupled to the gantry arm and the other of the half portions of the first frame.

2. The X ray computed tomography apparatus of claim 1, wherein the other half portion is a portion of the first frame that is located below the horizontal axis.

3. The X ray computed tomography apparatus of claim 2, wherein the other half portion is a portion of the first frame that is located at a height of not more than 1,000 mm from the floor surface, of the first frame.

4. The X ray computed tomography apparatus of claim 1, further comprising a cover configured to cover a half portion of the rotating unit that is located below the horizontal axis, wherein the second frame is provided between the cover and the rotating unit.

5. The X ray computed tomography apparatus of claim 1, wherein the second frame has a bent portion to avoid interference with the rotating unit.

6. The X ray computed tomography apparatus of claim 1, wherein a coupling portion between the gantry arm and the second frame has a planar shape.

7. The X ray computed tomography apparatus of claim 1, wherein a coupling portion between the first frame and the second frame has a planar shape.

8. The X ray computed tomography apparatus of claim 1, further comprising a third frame provided on an edge portion of the first frame that is located below the horizontal axis.

9. The X ray computed tomography apparatus of claim 1, wherein the gantry arm supports the rotating unit so as to allow the rotating unit to tilt around the horizontal axis.

10. An X ray computed tomography apparatus, comprising:
    an annular rotating unit on which an X ray tube and an X ray detector are configured to be mounted;
    a first frame configured to support the rotating unit so as to allow the rotating unit to rotate about a rotation axis;
    a base stand configured to support the first frame from a floor surface; and
    a gantry arm coupled to the base stand and the first frame and including a first portion having a bent structure configured to be coupled to one of half portions of the first frame divided by a horizontal axis perpendicular to the rotation axis and a second portion having a bent structure configured to be coupled to the other of the half portions of the first frame.

11. An X ray computed tomography apparatus, comprising:
    an annular rotating unit on which an X ray tube and an X ray detector are configured to be mounted;
    a first frame configured to support the rotating unit so as to allow the rotating unit to rotate about a rotation axis;
    a base stand configured to support the first frame from a floor surface; and
    a gantry arm having a bent structure configured to couple one of half portions of the first frame divided by a horizontal axis perpendicular to the rotation axis to the base stand,
    wherein the one of the half portions of the first frame has a bent structure configured to be coupled to the gantry arm.

* * * * *